(12) United States Patent
Linares et al.

(10) Patent No.: US 8,814,945 B2
(45) Date of Patent: Aug. 26, 2014

(54) IMPLANTABLE WRIST JOINT ASSEMBLY WITH SPHERICAL INTER-SUPPORT

(71) Applicants: Miguel A. Linares, Bloomfield Hills, MI (US); Linares Medical Devices, LLC, Auburn Hills, MI (US)

(72) Inventors: Miguel A. Linares, Bloomfield Hills, MI (US); Miguel A. Linares, Jr., Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 64 days.

(21) Appl. No.: 13/629,692

(22) Filed: Sep. 28, 2012

(65) Prior Publication Data

US 2013/0090738 A1 Apr. 11, 2013

Related U.S. Application Data

(60) Provisional application No. 61/540,231, filed on Sep. 28, 2012.

(51) Int. Cl.
*A61F 2/42* (2006.01)
*A61F 2/30* (2006.01)

(52) U.S. Cl.
CPC ..... *A61F 2/4261* (2013.01); *A61F 2002/30242* (2013.01); *A61F 2002/30014* (2013.01); *A61F 2002/30224* (2013.01); *A61F 2002/30253* (2013.01); *A61F 2002/30563* (2013.01); *A61F 2002/3064* (2013.01); *A61F 2002/30642* (2013.01); *A61F 2002/30878* (2013.01); *A61F 2001/30971* (2013.01); *A61F 2002/4264* (2013.01)
USPC .................... 623/21.13; 623/21.14

(58) Field of Classification Search
CPC .......... A61F 2/4261; A61F 2002/4261; A61F 2002/4264; A61F 2002/4266; A61F 2002/4269; A61F 2002/4289; A61F 2002/4292
USPC ............................................ 623/21.12–21.14
See application file for complete search history.

(56) References Cited

U.S. PATENT DOCUMENTS

| 5,458,646 | A | 10/1995 | Giachino et al. |
| 7,077,867 | B1 * | 7/2006 | Pope et al. ................. 623/20.14 |
| 2003/0187511 | A1 | 10/2003 | Ball et al. |
| 2006/0030946 | A1 | 2/2006 | Ball et al. |

FOREIGN PATENT DOCUMENTS

EP 0 820 731 B1 * 5/2003 ............. A61B 17/70

* cited by examiner

*Primary Examiner* — David H Willse
(74) *Attorney, Agent, or Firm* — Gifford, Krass, Sprinkle, Anderson & Citkowski, P.C.; Douglas J. McEvoy

(57) ABSTRACT

A multi-component wrist joint assembly incorporated into reconditioned end surfaces established between an upper radius bone and at least opposing lower scaphoid and lunate bones. A first component is anchored into the upper radius reconditioned end surface and exhibiting a first exposed support surface. A second component is anchored into the lower scaphoid and lunate reconditioned end surfaces and exhibiting a second exposed support surface. A spherical shaped intermediate component is supported in at least one of eccentric or rotational fashion between the first and second anchored components.

17 Claims, 6 Drawing Sheets

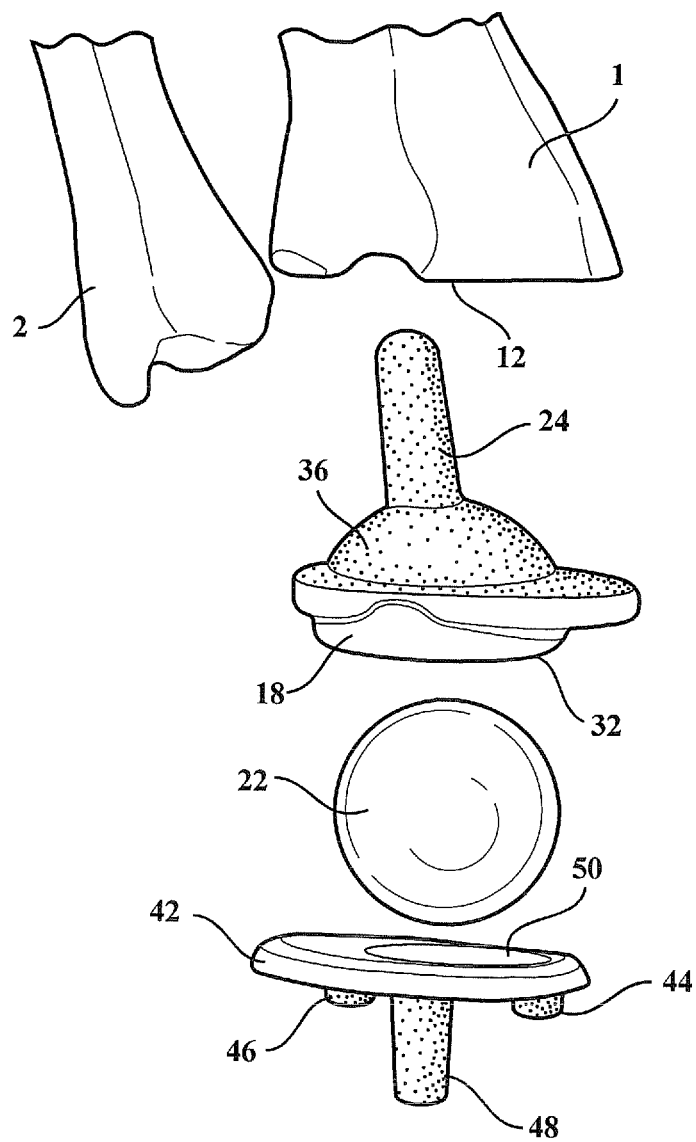
FIG. 4
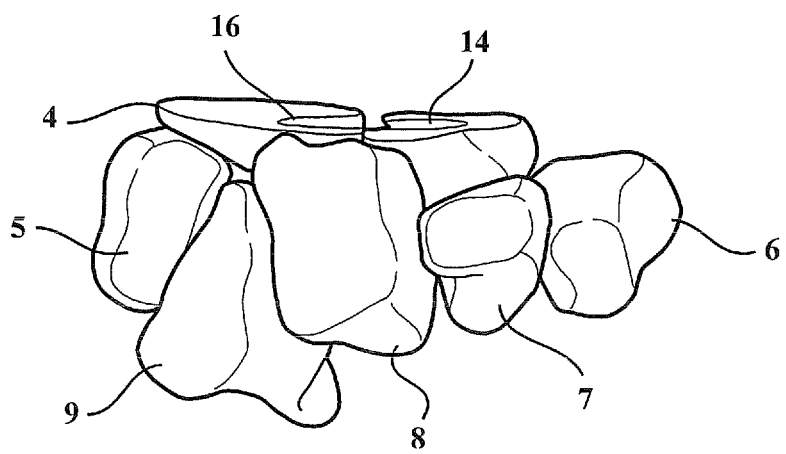

//* IMPLANTABLE WRIST JOINT ASSEMBLY WITH SPHERICAL INTER-SUPPORT

CROSS REFERENCE TO RELATED APPLICATIONS

The present application claims the priority of U.S. Ser. No. 61/540,231 filed Sep. 28, 2012.

FIELD OF THE INVENTION

The present invention discloses an artificial joint assembly, such as is particularly configured for employing as a retrofit wrist joint, and which combines multiple artificial components incorporated into first and second reconditioned joint defining surfaces for providing increased wear life in tandem with evenly distributed wear pattern/profile as well as enhanced flexibility and mobility.

BACKGROUND OF THE RELEVANT ART

The prior art is documented with various examples of wrist prostheses, one example of which is set forth in Ball et al. (US 2003/0187511 and US 2006/0030946) and which includes first, second and third components that in one form are radial, metacarpal and bearing components. A further example of a wrist prosthesis is depicted in U.S. Pat. No. 5,458,646, to Giachino, which discloses a distal and proximal supports associated with the radius and ulna bones. An intermediate component is depicted by a receptacle portion distally defining a concave bearing surface, such as which is supported by an ellipsoidal convex bearing surface having a generally part-circular cross-section associated with a proximal side of the distal part.

SUMMARY OF THE PRESENT INVENTION

The present invention discloses a multi-component wrist joint assembly incorporated into reconditioned end surfaces established between an upper radius bone and at least opposing lower scaphoid and lunate bones. The assembly includes a first component anchored into the upper radius reconditioned end surface and exhibiting a first exposed support surface. A second component is anchored into the lower scaphoid and lunate reconditioned end surfaces and exhibiting a second exposed support surface. An intermediate component is supported in at least one of eccentric or rotational fashion between the first and second anchored components.

Additional features include the intermediate component exhibiting a spherical shaped component. Each of the anchored components may further exhibit a concave surface for supporting the intermediate component, with each of the first, second and intermediate components being constructed of any of metal, plastic, polymer (including rubberized) or composite materials.

The spherical shaped component may also include a multi-layer composition with a softer outer layer and at least one harder interior layer. This can further include first and second inner layers of the spherical component establishing an eccentric rotational interface therebetween.

In a further variant, a plurality of surface projecting bearings are mounted within an innermost spherical shaped portion of the spherical component for facilitating the eccentric rotational interface. In a further variant, a grid pattern of lubricating grooves can be defined in a surface of an innermost spherical shaped portion of the spherical component for facilitating the eccentric rotational interface.

BRIEF DESCRIPTION OF THE DRAWINGS

Reference will now be made to the attached drawings, when read in combination with the following detailed description, wherein like reference numerals refer to like parts throughout the several views, and in which:

FIG. 4 is an exploded view of the implant assembly of FIG. 3 and substantially as described in the related variant of FIG. 2, with the exception of shallow lower implant anchors associated with the hand bones for providing improved hand mobility;

DETAILED DESCRIPTION OF THE PREFERRED EMBODIMENTS

As will be disclosed with succeeding reference to the several depicted embodiments, the present invention discloses an artificial joint assembly, such as is particularly configured for employing as a retrofit wrist joint, and which combines multiple artificial components incorporated into first and second reconditioned joint defining surfaces for providing increased wear life in tandem with evenly distributed wear pattern/profile as well as enhanced flexibility and mobility.

The joint assemblies described herein are particularly configured for such as in situ reconditioned installation within a patient's wrist joint (existing between lower facing end of the lower arm defined by radius and proximately located ulna bones) and corresponding upper ends of the lower lunate and scaphoid bone which defines an uppermost connecting location of a number of interconnected bones collectively defining the hand). It is further understood that certain applications could in theory include other joint applications, either human or other mammalian.

Also, and for purposes of ease and clarify of illustration, the various embodiments depicted further do not include reference to additional necessary components of the wrist joint, such as including associated muscles, tendons and ligaments, the inclusion of which are assumed and which collectively define a functioning and articulating wrist. A recitation of the associated ligament structure further includes, without limitation, such as the volar radio-carpal ligament, distal radio-ulnar liagement, radial collateral ligament, volar intercarpal ligaments, pisohamate ligament, pisometacarpal ligament, greater multangular capsular ligament, capsular ligament (thumb) and volar ligaments 2-5 (fingers), these extending at locations between the upper radius and ulna and lower collection of hand bones.

Figure 1:
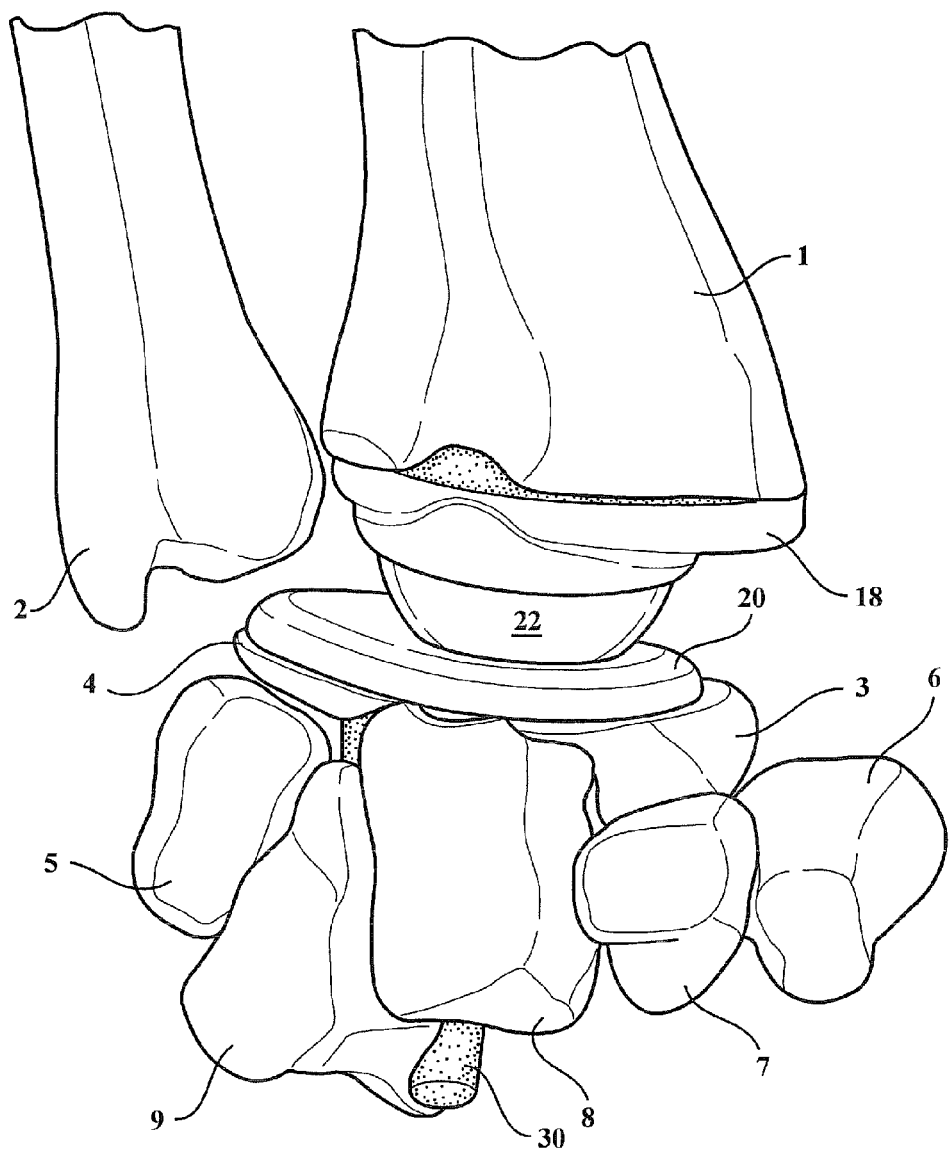
FIG. 1 is a perspective view of a wrist implant assembly according to the invention.

Referring now to FIG. 1, a perspective view is generally shown at 10 of a wrist implant assembly according to an embodiment the invention and which is incorporated between an upper positioned radius 1 and ulna 2 bones and a collection of lower opposing bones collectively defining the patient's hand and again including an uppermost and wrist joint defining scaphoid 3 (one of the carpal bones of the wrist situated between the hand and forearm on the thumb/lateral side) and lunate 4 (deep concavity with crescentic outline in center of proximal row of carpus or wrist between forearm and hand). An additional however incomplete recitation of additional hand bones depicted in each of FIGS. 1-4 further includes the triquetral bone 5 (located in wrist on medial side of proximal row of carpus between lunate and pisoform bones), pisiform bone (not shown but exhibiting small, knobbly and pea shape located on proximal row of carpus where ulna joins wrist), trapezium bone 6 (located at radial side of carpus between scaphoid and first metacarpal bone), and trapezoid bone 7 (smallest bone on distal row with wedge shape with broad dorsal end, narrow palmar surface end and four articular facets). Additional bones include the capitate bone 8 (largest of the carpal bones occupying center of wrist) and, finally, hamate bone 9 (wedge shaped with hook-like process projecting from volar surface located at medial and lower angle of carpus, with base facing downward and resting on fourth and fifth metacarpal bones, with upward/lateral-ward directed apex).

Having described in some detail the bone construction of the lower arm and hand defining the wrist proximate joint, reference is again made to FIG. 2 referencing in situ reconditioning of the bone ends, illustrated by conditioned end profile 12 configured into the bottom most end surface of the radius 1, as well as opposing upper end facing and recessed/reconditioned profiles 14 and 16 defined in the upper most opposing facing ends of the scaphoid 3 and lunate 4. According to one non-limiting surgical procedure, such in situ reconditioning can occur following incision or removal of any remaining damaged bone and/or cartilage associated with the damaged joint and during an appropriate surgical procedure utilizing medical drilling, boring and shaping instruments in order to recondition the joint defining bone ends and to create the desired shaping and profile of the joint. As previously indicated, it is advantageous to refashion the joint end profiles in situ during an appropriate surgical procedure, a further objective being to retain or repair, where possible, natural ligament, cartilage and muscle associated with a normal functioning joint.

Although not shown, such reconditioning can be employed with minimal interference to such necessary additional elements of the wrist joint including associated ligaments, muscles and tendons. Without limitation, it is further understood that the joint assemblies described in each of the illustrated variants can be integrated into either of human or synthetic bones (such as which can also contemplate both human and synthetic bones in a single joint application), with such joint assemblies also capable of surgically implanted in either total or partial fashion concurrent with any necessary degree of refashioning or removal of damaged bone or joint.

A set of bone end installable implant portions are depicted at 18 and 20 with each exhibiting a rear facing profile suitable for anchoring into the respective reconditioned end face configurations 12 and 14 & 16 defined in the radius 1 and scaphoid 3/lunate 4, respectively. The ulna bone 2 is further shown in a generally original arrangement with the further understanding that a suitable reconditioning of its associated end with the lateral offset position of the radius can also be reconditioned to some degree as is necessary.

Each of the implant portions 18 and 20 are constructed of any arrangement of metal, polymer, plastic, composite or other suitable material, with it further being understood that the individual pairs of components can be arrayed with any pattern of alternating materials, such that the components 18 and 20 being constructed of a first material, with an intermediate and inter-positioned spherical shaped bearing or ball portion 22 positioned therebetween and being constructed of a second alternating material. Although depicted as a spherical shaped element, the present invention contemplates the wrist joint including any potentially reconfigurable opposing recessed profiles associated with implant portions 18 and 20, and which may further be provided in combination with an alternately (i.e. non-spherical) shaped intermediate component including any type of cylindrical, pseudo cylindrical, oblong, oval ellipsoidal or other smooth shape. In this fashion, the desired wear properties and profiles are adjusted in part based upon the material selection of the individual components with concurrent objectives being both equalization of overall wear patterns established between the respective pairs of components and determining those situations in which metal on metal or plastic on plastic contact between the components is either desired or, more often, not.

A suitable medical adhesive, cement or other fastener can be employed for securing each of the upper implant component 18 and lower implant component 20 into the respective reconditioned joint defining end surfaces 12 of the radius 1 and 14/16 of the scaphoid 3 and lunate 4, respectively. As further best shown in FIG. 2, each of the reconditioned bone ends includes an interior extending aperture (best shown in shallow perspective by central apertures associated with recess profiles 14 and 16) and which are formed by a suitable bone drill in order to seat integrally formed and rearward extending anchoring stems including that depicted at 24 associated with a rear mounting profile of the upper insert 18 into the lower end of the radius 1, as well as the combination of lateral lower stems 26 and 28 (seating within scaphoid 3 and lunate 4) and intermediate deep anchor 30 (for mounting between capitate 8 and hamate 9) in a manner so that the extending end of the deep anchor 30 seats within a base location of an associated middle finger digit (bone).

Each of the end face mounted implants 18 and 20 further exhibits a concave exterior facing profile and which includes a more pronounced and substantially hemi-spherical concavity 32 (FIG. 2) defined in the upper insert 18, with an opposing and lesser pronounced/shallower concave seating cavity 34 associated with the lower insert 20. Upon securing the implants 18 and 20 within the reconditioned end face locations 12 and 14 & 16 of the bones 1 and 3 & 4, these collectively define upper and lower seating locations for supporting the interposed spherical element 22 as best depicted in perspectives of FIG. 1 in a designed range of eccentric articulating ranges as permitted by the joint construction. As further previously noted, the concave shaped recess profiles can each be constructed of a smooth lubricant entrained or other polished plastic, composite or metal surface, with the exterior configuration of the spherical support 22 again being constructed of an alternating material, such as to reduce and equalize wear profiles, as well as to enhance operational range and effectiveness.

Figure 2:
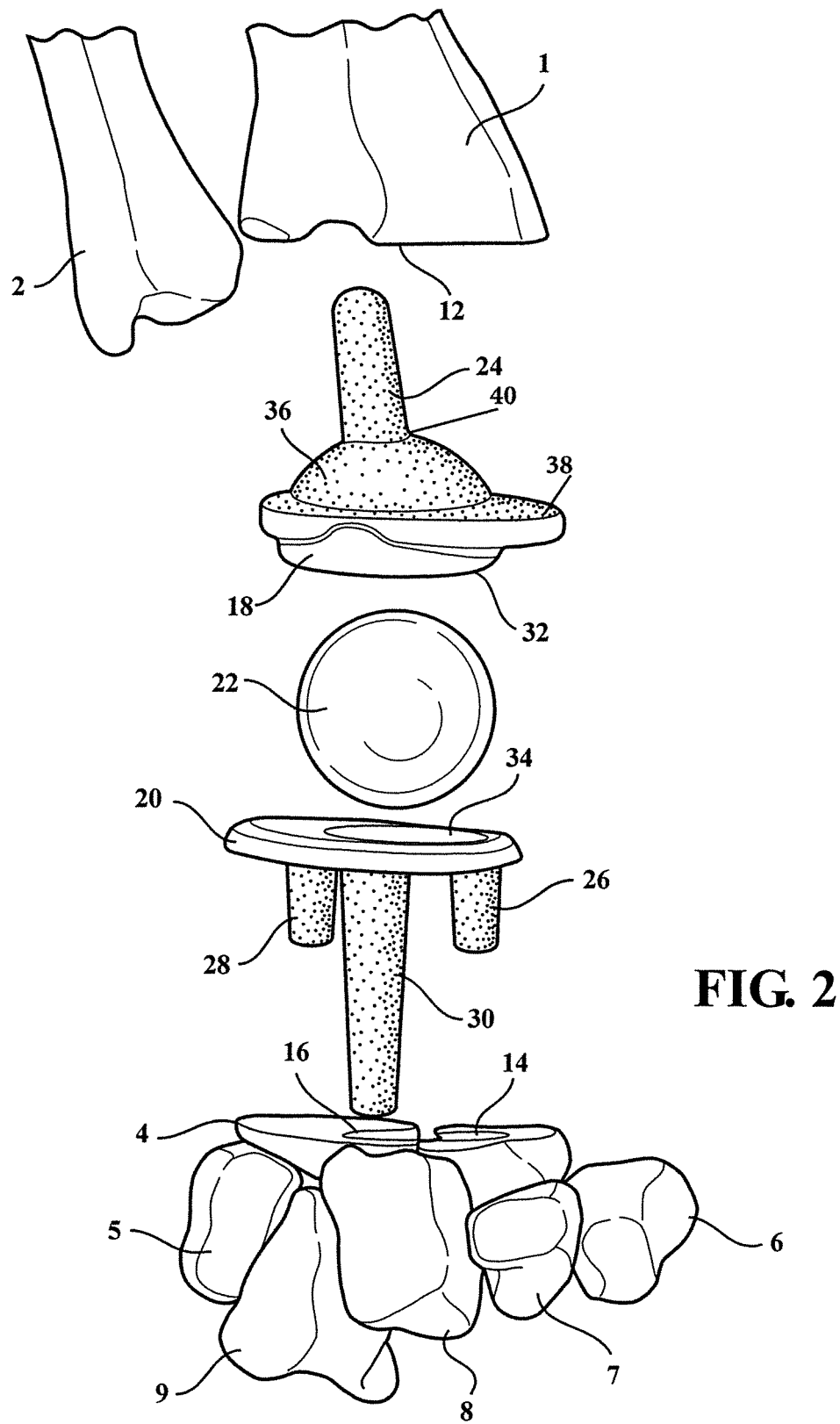
FIG. 2 is an exploded view of the wrist implant assembly of FIG. 1 and better illustrating the reconditioned end-configurations established between the lower arm radius bone and collection of hand bones including the lunate, scaphoid and capitates bones, combined with end face seating and marrow growth promoting implant support inserts with deep anchorage features in combination with intermediate positioned and eccentrically supported spherical portion.

As again previously indicated, additional configurations of muscles, ligaments, tendons are provided and can include both natural and/or synthetic materials which can be implanted or reconstructed in order to provide a dynamic and long-term implantable assembly. As shown in FIG. 2, the seating or inserting rear faces of the upper mounted implant portion 18 (including rear base convex surface 36 side of upper implant 18 defining an outer lip edge 38 with the perimeter of the implant 18 at a shallowest end and converging to inwardly extending stem 24 in a deepening direction defined by interface 40) and further opposing implant portion 20 (including each of posts 26 and 28 and central deep anchor 30) can each further include an undercut textured or otherwise roughened consistency, this contributing to promotion of bone marrow in-growth into the implant portions following such as initial adhesive and seating affixation, such bone growth contributing to long term retention of the implant.

Figure 3:
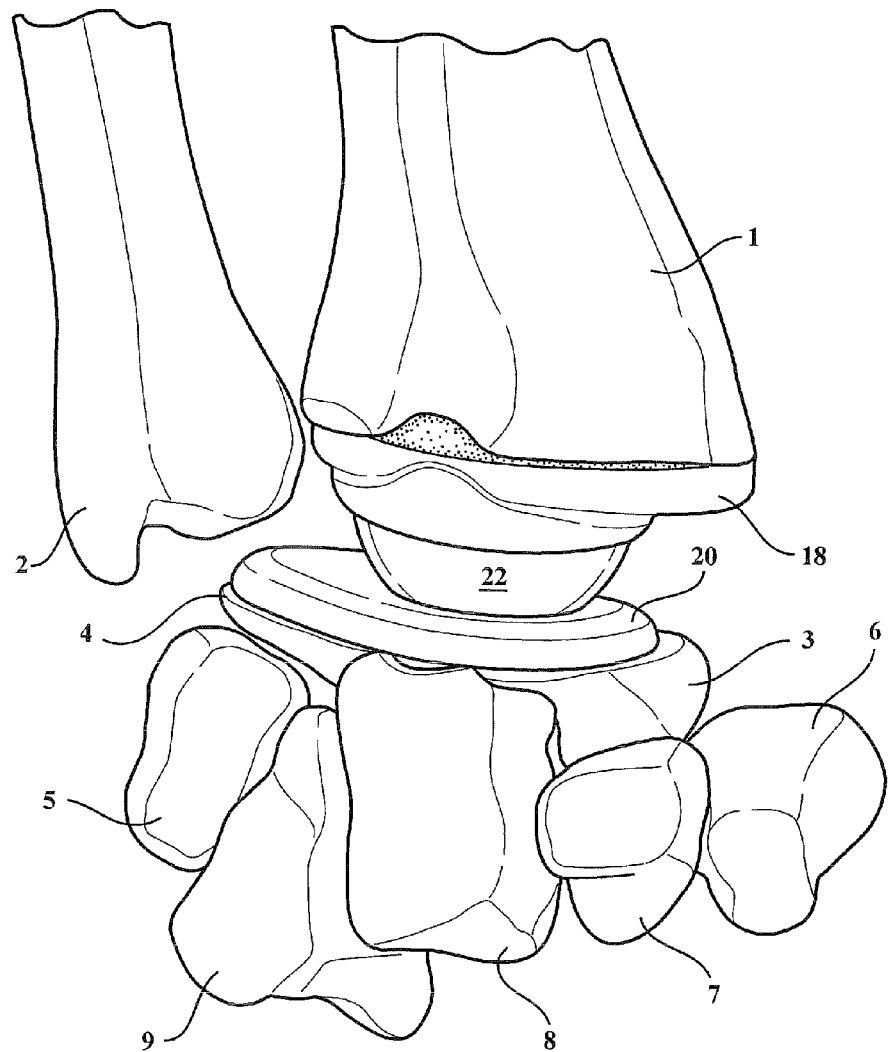
FIG. 3 is a perspective view of a wrist implant assembly according to a sub-variant of FIG. 1.

FIGS. 3 and 4 depict a substantially identical variant to that shown in FIGS. 1-2, with the exception that the second lower implant is reconfigured as shown at 42 differs from that previously described at 20 in FIG. 2 in that it depicts a shallower arrangement of mounting posts, including outer lateral posts 44 and 46 seating within reduced depth apertures formed in scaphoid 3 and lunate 4, along with a more modestly deeper central anchor 48 (such as less than one half the overall depth of deep anchor 30) and which results in enhanced hand mobility by virtue of seating more shallowly into the hand bones short of the middle finger base digit. Lower implant 42 otherwise includes a suitable configured concave upper surface 50, which can be similar in dimension to that previously described at 34 in FIG. 2 and which, in combination with the upper deepened concavity profile 32 associated with the upper implant 18, supports the inter-spherical element 22 in substantially identical fashion (see FIG. 3) as compared to as shown in FIG. 1.

Figure 5:
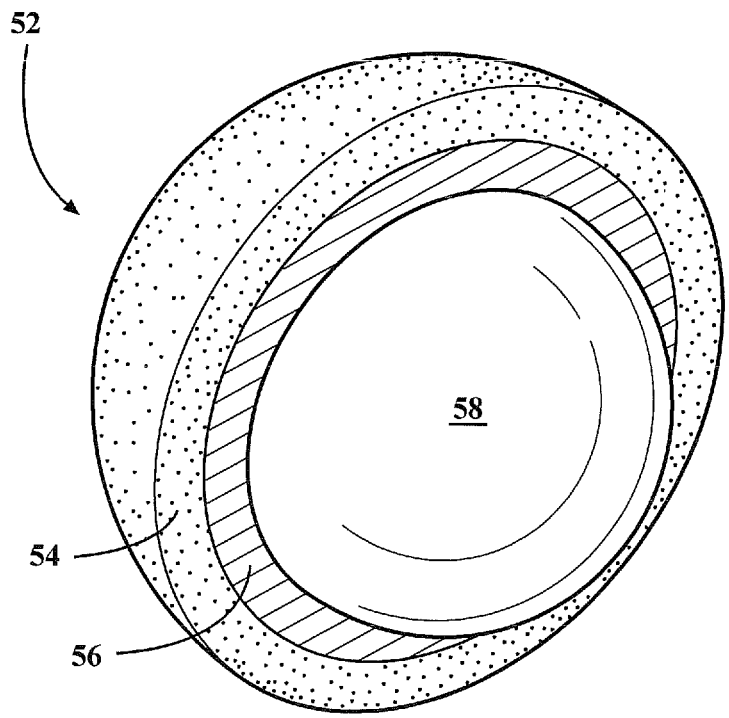
FIG. 5 is a pseudo cutaway view of a spherical shaped intermediate support and which illustrates its multi-material construction with softer outermost shell material and intermediate harder material in cutaway, combined with innermost harder core material in spherical perspective and which further evidences an eccentric rotatable interface established between said intermediate and innermost layers.

Referring now to FIG. 5, a cutaway view is generally shown at 52 of a selected spherical inter-movable support, such as again represented by the spherical ball disclosed in the preceding described variant of FIG. 1. The pseudo cutaway view of FIG. 5 illustrates one non-limiting example of a multi-layer material construction and which includes a softer (typically plastic or plastic composite) outermost material layer 54, an intermediate harder 56 material (typically another plastic), and an innermost harder material 58 (which is depicted in un-sectioned spherical perspective shape and can be of a similar hardness as the intermediate layer 56 as well as potentially including either of a relatively harder or softer material based on the specifics and preferences of the application).

In operation, an eccentric rotatable interface is established between the intermediate 56 and innermost (or core) 58 layers, this typically arising from the compressive aspects exerted on the softest outer shell layer 54 by both the upper and lower associated implants resulting in a degree of inter-rotative offset or eccentric give or play established at the interior interface boundary between the intermediate layer 56 and the inner core 58. The outer compressive exerted forces typically result from any inwardly angular directed force exerted on the intermediate spherical element, and such as is defined as a non-tangential force.

Figure 6:
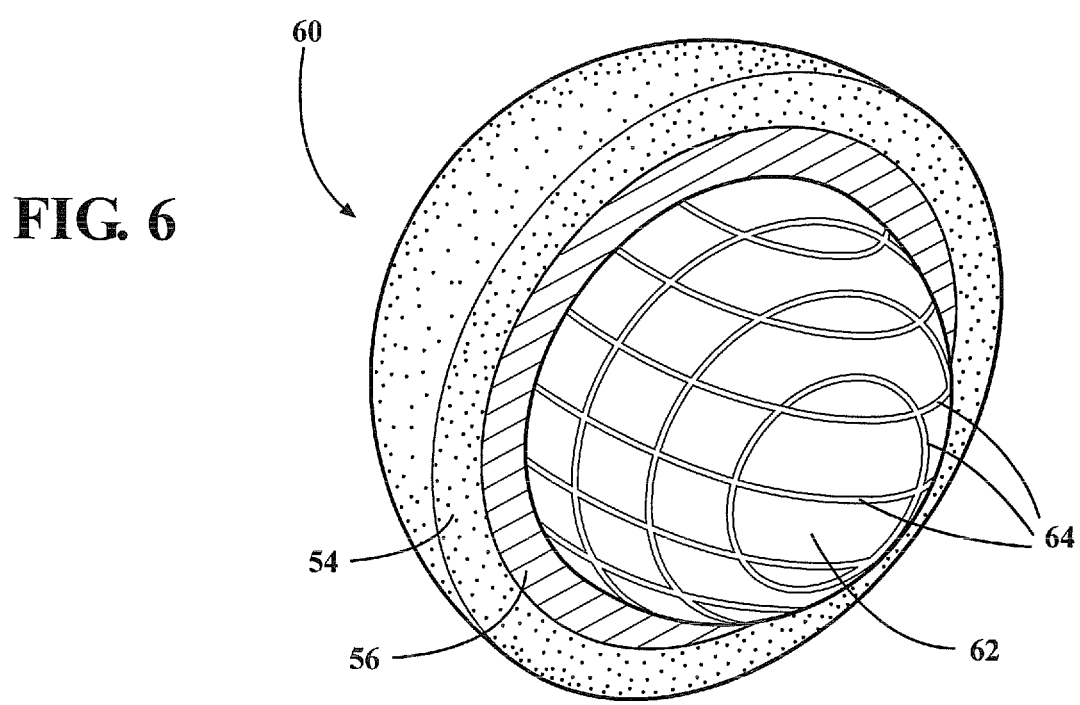
FIG. 6 is a pseudo cutaway view of a spherical shaped intermediate support similar to that in FIG. 5 and further depicting a plurality of lubricant supporting grooves defined in a surface grid pattern associated with the innermost hardened core.

FIG. 6 is a similar pseudo cutaway view, generally at 60, of a spherical shaped intermediate support similar to that in FIG. 5, with identical outer soft shell 54 and intermediate harder shell 56, and in which an innermost core is reconfigured as shown at 62 with a grooved arrangement 64. The grooves 64 can facilitate eccentric motion in the interior boundary defined between layers 56 and 62, in the manner previously described, and/or can also includes entrainment of a volume of lubricant supported within the grooves 64 in a fairly evenly distributed fashion associated with the hardened core 62.

It is also envisioned and understood that the spherical ball, grooves or other supporting structure can include small entrapment channels or pockets for retaining micro particles of debris, either or both plasticized resulting from wear of the implant portions and bone, and such as is further defined as debris osteolysis. The ability to segregate and remove such micro particles (again using the pattern of grooves 64 or other suitable arrangement) assists in extending useful life of the implant along with reducing pain, squeak/noise or other undesirable aspects typical of previous implant designs.

Figure 7:
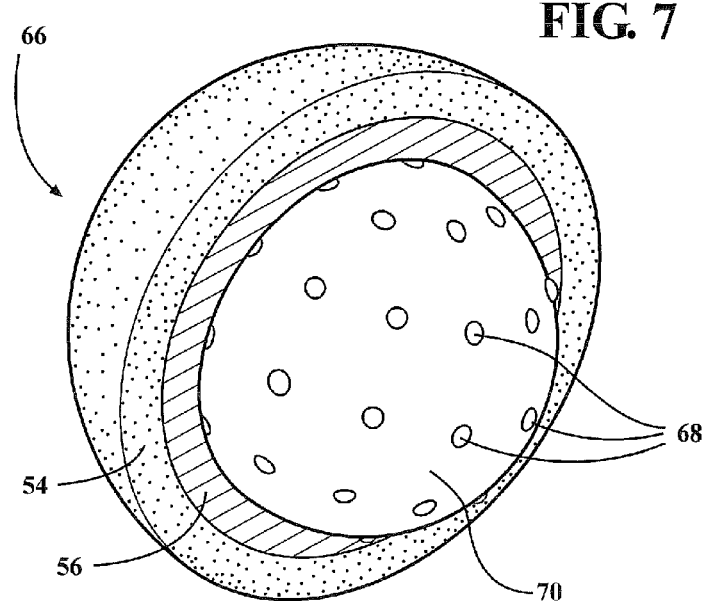
FIG. 7 is a further cutaway view which is again similar to FIG. 5 and further depicting a plurality of substantially surface embedded ball bearings associated with the inner most core.
Figure 8:
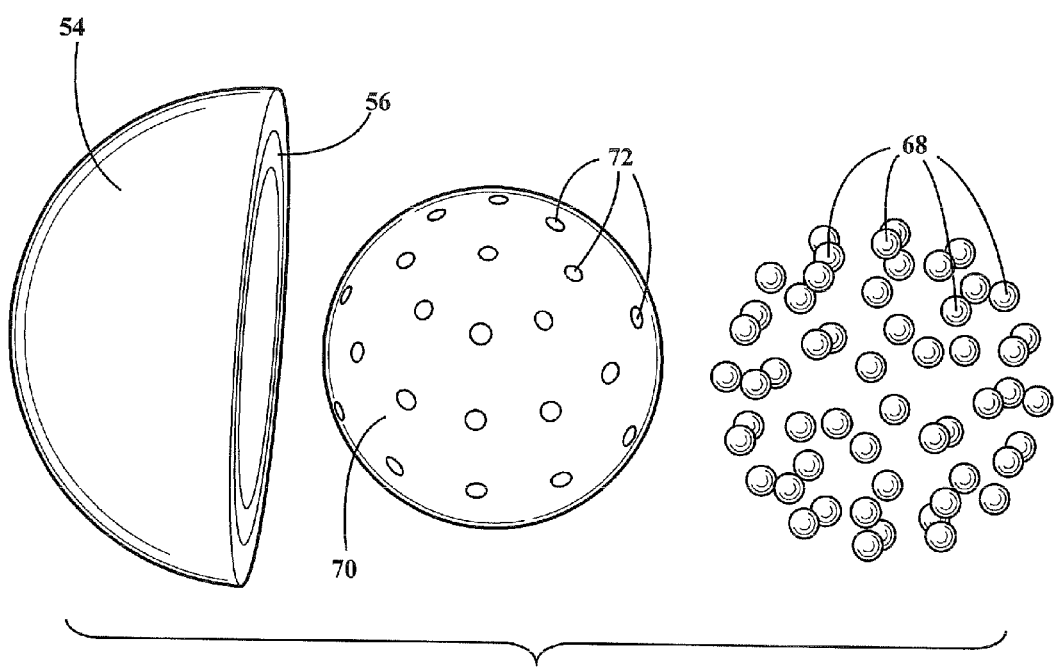
FIG. 8 is an exploded view of the cutaway of FIG. 7 and which better illustrates the arrangement of micro sized ball bearings in combination with the seating locations arranged about the spherical exterior surface of the harder core material.

Referring now to FIG. 7, a further cutaway view is generally shown at 66 which is again similar to FIG. 5 and further depicting a plurality of substantially surface embedded ball bearings 68 (such as constructed of any of a metal, plastic or other suitable material) associated with a further redesigned version of an inner most core 70. As best depicted in the further exploded view of FIG. 8, the ball bearings 68 are separated from the hardened inner spherical core 70, thereby revealing substantially spherical shaped pockets 72 defined across the exterior profile of the core 70 and which substantially seat the individual bearings 68 in a manner which permits the tips thereof (again FIG. 7) to project in a manner which facilitates additional eccentric support motion with respect to the interior interface boundary established with the intermediate later 56 in a manner consistent with the dynamic environments referenced in relation to FIGS. 5 and 7.

Having described my invention, other and additional preferred embodiments will become apparent to those skilled in the art to which it pertains, and without deviating from the scope of the appended claims.

I claim:

1. A multi-component wrist joint assembly incorporated into reconditioned end surfaces established between an upper radius bone and at least opposing lower scaphoid and lunate bones, said assembly comprising:
   a first component adapted to being anchored into the upper radius reconditioned end surface and exhibiting a first exposed and substantially hemi-spherical concave support surface;
   a second component adapted to being anchored into the lower scaphoid and lunate reconditioned end surfaces and exhibiting a second exposed and substantially hemi-spherical concave support surface; and
   a spherical shaped component supported in seated fashion within each of said concave support surfaces and between said first and second components, such that said spherical shaped component establishes each of eccentric and rotational articulation separately with said first and second anchored components.

2. The joint assembly as described in claim 1, each of said first, second and spherical shaped components further being constructed of at least one of a metal, plastic, polymer or composite material.

3. The joint assembly as described in claim 1, said spherical shaped component further comprising a multi layer composition including a softer outer layer and at least one harder interior layer.

4. The joint assembly as described in claim 3, further comprising first and second inner layers of said spherical component establishing an eccentric rotational interface therebetween.

5. The joint assembly as described in claim 4, further comprising a plurality of surface projecting bearings mounted within an innermost spherical shaped portion of said spherical component facilitating said eccentric rotational interface.

6. The joint assembly as described in claim 4, further comprising a grid pattern of lubricating grooves defined in a surface of an innermost spherical shaped portion of said spherical component facilitating said eccentric rotational interface.

7. A multi-component wrist joint assembly incorporated into reconditioned end surfaces established between an upper radius bone and at least opposing lower scaphoid and lunate bones, said assembly comprising:
   a first component having a rear mounting profile including a base convex surface, a stem extending beyond an interface with said convex surface in a deepening direction and such that said first component is adapted to being anchored into a matching negative profile associated with the upper radius reconditioned end surface, said first component exhibiting a first exposed support surface;
   a second component having a rear mounting profile including a plurality of stems extending in a deepening direction and adapted to being anchored into matching negative profiles associated with the lower scaphoid and lunate reconditioned end surfaces, said second component exhibiting a second exposed support surface;
   a spherical shaped intermediate component supported in each of eccentric and rotational articulation separately with said first and second anchored components; and
   each of said anchored components further exhibiting a concave surface for supporting said intermediate component.

8. The joint assembly as described in claim 7, each of said first, second and intermediate components further being constructed of at least one of a metal, plastic, polymer or composite material.

9. The joint assembly as described in claim 7, said spherical shaped component further comprising a multi layer composition including a softer outer layer and at least one harder interior layer.

10. The joint assembly as described in claim 9, further comprising first and second inner layers of said spherical component establishing an eccentric rotational interface therebetween.

11. The joint assembly as described in claim 10, further comprising a plurality of surface projecting bearings mounted within an innermost spherical shaped portion of said spherical component facilitating said eccentric rotational interface.

12. The joint assembly as described in claim 10, further comprising a grid pattern of lubricating grooves defined in a surface of an innermost spherical shaped portion of said spherical component facilitating said eccentric rotational interface.

13. A multi-component wrist joint assembly incorporated into reconditioned end surfaces established between an upper radius bone and at least opposing lower scaphoid and lunate bones, said assembly comprising:
   a first component having a rear mounting profile including a base convex surface further defining an outer lip edge associated with a perimeter of said first component, a stem extending beyond an interface with said convex surface in a deepening direction and such that said first component is adapted to being anchored into a matching negative profile associated with the upper radius reconditioned end surface, said first component exhibiting a first exposed and substantially hemi-spherical concave support surface;
   a second component having a rear mounting profile including a plurality of stems extending in a deepening direction and adapted to being anchored into matching negative profiles associated with the lower scaphoid and lunate reconditioned end surfaces, said second component exhibiting a second exposed and substantially hemi-spherical concave support surface; and
   a spherical shaped intermediate component supported in each of eccentric and rotational articulation separately with said first and second anchored components, said spherical shaped component further having a multi-layer composition including a softer outer layer and at least one harder interior layer.

14. The joint assembly as described in claim 13, each of said first, second and intermediate components further being constructed of at least one of a metal, plastic, polymer or composite material.

15. The joint assembly as described in claim 13, further comprising first and second inner layers of said spherical component establishing an eccentric rotational interface therebetween.

16. The joint assembly as described in claim 15, further comprising a plurality of surface projecting bearings mounted within an innermost spherical shaped portion of said spherical component facilitating said eccentric rotational interface.

17. The joint assembly as described in claim 15, further comprising a grid pattern of lubricating grooves defined in a surface of an innermost spherical shaped portion of said spherical component facilitating said eccentric rotational interface.

* * * * *

UNITED STATES PATENT AND TRADEMARK OFFICE
CERTIFICATE OF CORRECTION

PATENT NO.        : 8,814,945 B2                                        Page 1 of 1
APPLICATION NO.   : 13/629692
DATED             : August 26, 2014
INVENTOR(S)       : Miguel A. Linares et al.

It is certified that error appears in the above-identified patent and that said Letters Patent is hereby corrected as shown below:

On the title page:

Item (60)   Related U.S. Application Data

Delete "2012", Insert --2011--

Signed and Sealed this
Fifth Day of May, 2015

Michelle K. Lee
*Director of the United States Patent and Trademark Office*